United States Patent [19]

Krenzer

[11] 4,046,554
[45] Sept. 6, 1977

[54] DIALKYL ACETALS OF ANILINOACETALDEHYDES

[75] Inventor: John Krenzer, Oak Park, Ill.

[73] Assignee: Velsicol Chemical Corporation, Chicago, Ill.

[21] Appl. No.: 679,628

[22] Filed: Apr. 23, 1976

Related U.S. Application Data

[62] Division of Ser. No. 530,797, Dec. 19, 1974, Pat. No. 3,966,811.

[51] Int. Cl.² ............................................. A01N 9/20
[52] U.S. Cl. ............................................... 71/118
[58] Field of Search ................................... 71/118

[56] References Cited

U.S. PATENT DOCUMENTS

| | | | |
|---|---|---|---|
| 3,071,613 | 1/1963 | Surrey | 260/562 B |
| 3,442,945 | 5/1969 | Olin | 71/118 X |
| 3,598,859 | 8/1971 | Yates et al. | 260/471 |
| 3,890,134 | 6/1975 | Teach | 71/118 X |

Primary Examiner—Lewis Gotts
Assistant Examiner—Catherine L. Mills

Attorney, Agent, or Firm—Robert J. Schwarz; Dietmar H. Olesch

[57] ABSTRACT

This invention discloses new compounds of the formula

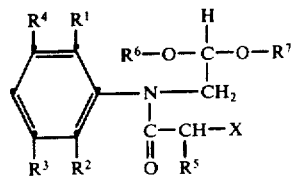

wherein $R^1$, $R^6$ and $R^7$ are each alkyl; $R^2$ is selected from the group consisting of hydrogen, alkyl, alkoxy and trifluoromethyl; $R^3$ and $R^4$ are each selected from the group consisting of hydrogen, lower alkyl, halogen, cyano, alkoxy, alkylthio, haloalkyl and alkoxyalkyl; $R^5$ is selected from the group consisting of hydrogen and alkyl; and X is halogen. The compounds of the above description are useful as herbicides.

9 Claims, No Drawings

DIALKYL ACETALS OF ANILINOACETALDEHYDES

This application is a division of co-pending application Ser. No. 530,797, filed Dec. 19, 1974 now U.S. Pat. No. 3,966,811, issued June 29, 1976.

This invention relates to new compositions of matter and more specifically relates to new chemical compounds of the formula

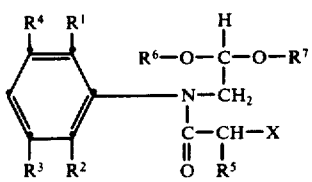
(I)

wherein $R^1$, $R^6$ and $R^7$ are each alkyl; $R^2$ is selected from the group consisting of hydrogen, alkyl, alkoxy and trifluoromethyl; $R^3$ and $R^4$ are each selected from the group consisting of hydrogen, lower alkyl, halogen, cyano, alkoxy, alkylthio, haloalkyl and alkoxyalkyl; $R^5$ is selected from the group consisting of hydrogen and alkyl; and X is halogen.

The compounds of the present invention are unexpectedly useful as herbicides.

In a preferred embodiment of this invention $R^1$, $R^6$ and $R^7$ are each lower alkyl; $R^2$ is selected from the group consisting of hydrogen, lower alkyl and lower alkoxy; $R^3$ and $R^4$ are each selected from the group consisting of hydrogen, lower alkyl, halogen, cyano, lower alkoxy, lower alkylthio, lower chloroalkyl, trifluoromethyl and lower alkoxyalkyl; $R^5$ is selected from the group consisting of hydrogen and lower alkyl; and X is selected from the group consisting of chlorine and bromine.

The term lower as used herein designates a straight or branched carbon chain of up to and including six carbon atoms.

The compounds of the present invention can be prepared by reacting a compound of the formula

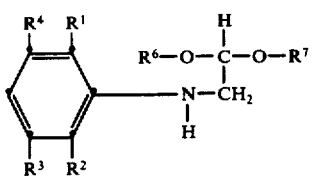
(II)

wherein $R^1$, $R^2$, $R^3$, $R^4$, $R^6$ and $R^7$ are as heretofore described, with an about equimolar amount of a compound of the formula

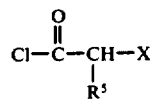
(III)

wherein $R^5$ and X are as heretofore described. This reaction can be effected by cooling a solution of the compound of formula II containing an acid acceptor, such as an alkali metal carbonate or tertiary amine, to a temperature of about 0° C. The compound of formula III can then be incrementally added with stirring. After the addition is completed the mixture can be allowed to warm to room temperature with continued stirring. The reaction mixture can then be filtered and washed with dilute aqueous acid. The washed filtrate can then be stripped of solvent to yield the desired product as the residue.

The compounds of formula II can be prepared by reacting a compound of the formula

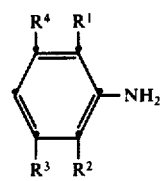
(IV)

wherein $R^1$, $R^2$, $R^3$ and $R^4$ are as heretofore described, with an acetal of the formula

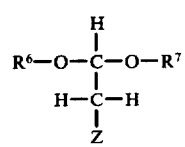
(V)

wherein Z is chlorine or bromine and $R^6$ and $R^7$ are as heretofore described. This reaction can be effected by combining the compounds of formulae IV and V in an inert organic reaction medium in the presence of an acid acceptor such as an alkali metal carbonate or a tertiary amine. The reaction mixture can then be heated at reflux for a period of from about 4 to about 48 hours. After this time the reaction mixture can be filtered and stripped of solvent to yield the desired product as the residue.

Exemplary compounds of formula V are the dimethyl acetal of 2-chloroacetaldehyde, the diethyl acetal of 2-bromoacetaldehyde, the dipropyl acetal of 2-chloroacetaldehyde, the dibutyl acetal of 2-chloroacetaldehyde, the dipentyl acetal of 2-chloroacetaldehyde, the dihexyl acetal of 2-bromoacetaldehyde, the methyl ethyl acetal of 2-chloroacetaldehyde, the methyl propyl acetal of 2-chloroactaldehyde, the ethyl hexyl acetal of 2-chloroacetaldehyde and the like.

Exemplary compounds of formula IV are 2,6-dimethylaniline, 2,6-diethylaniline, 2,6-dipropylaniline, 2,6-dibutylaniline, 2,6-dihexylaniline, 2-methylaniline, 2-ethylaniline, 2-propylaniline, 2-butylaniline, 2-pentylaniline, 2-hexylaniline, 2-methoxy-6-methylaniline, 2-methoxy-6-ethylaniline, 2-ethoxy-6-ethylaniline, 2-propoxy-6-methylaniline, 2-butoxy-6-ethylaniline, 2-hexyloxy-6-methylaniline, 2,3,6-trimethylaniline, 2,3,6-triethylaniline, 2,3,6-tripropylaniline, 2,6-dimethyl-4-butylaniline, 2,5-diethylaniline, 2-methyl-5-chloroaniline, 2-methyl-5-bromoaniline, 2-methyl-3-iodoaniline, 2,6-diethyl-3-fluoroaniline, 2-methyl-6-trifluoromethylaniline, 2-methyl-3-chloroaniline, 2-methyl-5-bromoaniline, 2-methyl-5-cyanoaniline, 2-methyl-5-methoxyaniline, 2-methyl-3-methylthioaniline, 2-methyl-5-trifluoromethylaniline, 2-methyl-5-methoxymethylaniline and the like.

Exemplary compounds of formula III are α-chloroacetyl chloride, α-bromoacetyl chloride, α-iodoacetyl chloride, α-chloropropionyl chloride, α-bromopropionyl chloride, α-chlorobutanoyl chloride, α-chloropentanoyl chloride, α-chlorohexanoyl chloride, α-chloroheptanoyl chloride, α-bromobutanoyl chloride and the like.

The manner in which the compounds of the present invention can be prepared is more specifically illustrated in the following examples.

EXAMPLE 1

Preparation of the Dimethyl Acetal of 2-(2,6-Dimethylanilino)acetaldehyde 2,6-Dimethylaniline (60 grams), the dimethyl acetal of 2-chloroacetaldehyde (25 grams) and sodium carbonate (21.2 grams) were charged into a glass reaction vessel equipped with a mechanical stirrer, thermometer and reflux condenser. The reaction mixture was heated at 150° C for a period of about 30 hours. After this time the mixture was filtered and the filtrate was distilled to yield the desired product the dimethyl acetal of 2-(2,6-dimethylanilino)acetaldehyde having a boiling point of 105° C at 1 mm of Hg pressure.

EXAMPLE 2

Preparation of the Dimethyl Acetal of 2-(N-α-Chloroacetyl-2,6-dimethylanilino)acetaldehyde The dimethyl acetal of 2-(2,6-dimethylanilino)-acetaldehyde (12.2 grams), triethylamine (8.1 ml) and benzene (50 ml) were charged into a reaction vessel equipped with a mechanical stirrer, thermometer and cooling means. The mixture was cooled to about 0° C and chloroacetyl chloride (4.4 ml) was incrementally added with stirring. After the addition was complete stirring was continued and the reaction mixture was permitted to warm to room temperature. After this time the mixture was filtered, washed with dilute hydrochloric acid and stripped of solvent under reduced pressure to yield the desired product the dimethyl acetal of 2-(N-α-chloroacetyl-2,6-dimethylanilino)acetaldehyde.

EXAMPLE 3

Preparation of the Diethyl Acetal of 2-(2,6-Diethylanilino)acetaldehyde 2,6-Diethylaniline (120 grams), the diethyl acetal of 2-chloroacetaldehyde (78.8 grams) and sodium carbonate (42.4 grams) were charged into a glass reaction vessel equipped with a mechanical stirrer, thermometer and reflux condenser. The reaction mixture was heated at 150° C for a period of about 30 hours. After this time the mixture was filtered and the filtrate was distilled to yield the desired product the diethyl acetal of 2-(2,6-diethylanilino)acetaldehyde having a boiling point of 130° C at 1 mm of Hg pressure.

EXAMPLE 4

Preparation of the Diethyl Acetal of 2-(N-α-Chloroacetyl-2,6-diethylanilino)acetaldehyde The diethyl acetal of 2-(2,6-diethylanilino)acetaldehyde (10.0 grams), sodium carbonate (4.0 grams) dissolved in water (50 ml) and benzene (50 ml) were charged into a reaction vessel equipped with a mechanical stirrer, thermometer and cooling means. The mixture was cooled to about 0° C and chloroacetyl chloride (3.0 ml) was incrementally added with stirring. After the addition was complete stirring was continued and the reaction mixture was permitted to warm to room temperature. After this time the mixture was filtered, washed with dilute hydrochloric acid and stripped of solvent under reduced pressure to yield the desired product the diethyl acetal of 2-(N-α-chloroacetyl-2,6-diethylanilino)acetaldehyde.

EXAMPLE 5

Preparation of the Diethyl Acetal of 2-(2,6-Dimethylanilino)acetaldehyde 2,6-Dimethylaniline (80 grams), the diethyl acetal of 2-bromoacetaldehyde (59.1 grams) and sodium carbonate (25.2 grams) were charged into a glass reaction vessel equipped with a mechanical stirrer, thermometer and reflux condenser. The reaction mixture was heated at 150° C for a period of about 30 hours. After this time the mixture was filtered and the filtrate was distilled to yield the desired product the diethyl acetal of 2-(2,6-dimethylanilino)acetaldehyde as a brown tarry solid.

EXAMPLE 6

Preparation of the Diethyl Acetal of 2-(N-α-Chloroacetyl-2,6-dimethylanilino)acetaldehyde The diethyl acetal of 2-(2,6-dimethylanilino)-acetaldehyde (13.0 grams), sodium carbonate (5.8 grams) dissolved in water (50 ml) and benzene (50 ml) were charged into a reaction vessel equipped with a mechanical stirrer, thermometer and cooling means. The mixture was cooled to about 0° C and chloroacetyl chloride (6.2 grams) was incrementally added with stirring. After the addition was complete stirring was continued and the reaction mixture was permitted to warm to room temperature. After this time the mixture was filtered, washed with dilute hydrochloric acid and stripped of solvent under reduced pressure to yield the desired product the diethyl acetal of 2-(N-α-chloroacetyl-2,6-dimethylanilino)-acetaldehyde.

EXAMPLE 7

Preparation of the Dimethyl Acetal of 2-(2,6-Diethylanilino)acetaldehyde 2,6-Diethylaniline (100 grams), the dimethyl acetal of 2-chloroacetaldehyde (37.5 grams) and sodium carbonate (31.8 grams) were charged into a glass reaction vessel equipped with a mechanical stirrer, thermometer and reflux condenser. The reaction mixture was heated at 150° C for a period of about 30 hours. After this time the mixture was filtered and the filtrate was distilled to yield the desired product the dimethyl acetal of 2-(2,6-dimethylanilino)acetaldehyde having a boiling point of 120° C at 1 mm of Hg pressure.

EXAMPLE 8

Preparation of the Dimethyl Acetal of 2-(N-α-Chloroacetyl-2,6-diethylanilino)acetaldehyde The dimethyl acetal of 2-(2,6-diethylanilino)acetaldehyde (13.0 grams), sodium carbonate (5.8 grams) dissolved in water (50 ml) and benzene (50 ml) were charged into a reaction vessel equipped with a mechanical stirrer, thermometer and cooling means. The mixture was cooled to about 0° and chloroacetyl chloride (6.2 ml) was incrementally added with stirring. After the addition was complete stirring was continued and the reaction mixture was permitted to warm to room temperature. After this time the mixture was filtered, washed with dilute hydrochloric acid and stripped of solvent under reduced pressure to yield the desired product the dimethyl acetal of 2-(N-α-chloroacetyl-2,6-diethylanilino)acetaldehyde.

EXAMPLE 9

Preparation of the Dimethyl Acetal of 2-(2,3,6-Trimethylanilino)acetaldehyde 2,3,6-Trimethylaniline (0.3 mole), the dimethyl acetal of 2-chloroacetaldehyde (0.3 mole) and sodium carbonate (20 grams) are charged into a glass reaction vessel equipped with a mechanical stirrer, thermometer and reflux condenser. The reaction mixture is heated at about 150° C for a period of about 8 hours. After this time the mixture is filtered and the filtrate is distilled to yield the desired product the dimethyl acetal of 2-(2,3,6-trimethylanilino)acetaldehyde.

EXAMPLE 10

Preparation of the Dimethyl Acetal of 2-(N-α-Bromopropionyl-2,3,6-trimethylanilino)acetaldehyde The dimethyl acetal of 2-(2,3,6-trimethylanilino)acetaldehyde (0.1 mole), sodium carbonate (0.06 mole) dissolved in water (50 ml) and benzene (50 ml) are charged into a glass reaction vessel equipped with a mechanical stirrer, thermometer and cooling means. The mixture is cooled to a temperature of about 0° C and α-bromopropionyl chloride (0.11 mole) is incrementally added with stirring. After the addition is completed stirring is continued and the reaction mixture is permitted to warm to room temperature. After this time the mixture is filtered, washed with dilute hydrochloric acid and stripped of solvent to yield the desired product the dimethyl acetal of 2-(N-α-bromopropionyl-2,3,6-trimethylanilino)acetaldehyde.

EXAMPLE 11

Preparation of the Dimethyl Acetal of 2-(2-Methyl-5-chloroanilino)acetaldehyde

2-Methyl-5-chloroaniline (0.3 mole), the dimethyl acetal of 2-chloroacetaldehyde (0.3 mole) and sodium carbonate (20 grams) are charged into a glass reaction vessel equipped with a mechanical stirrer, thermometer and reflux condenser. The reaction mixture is heated at about 150° C for a period of about 8 hours. After this time the mixture is filtered and the filtrate is distilled to yield the desired product the dimethyl acetal of 2-(2-methyl-5-chloroanilino)acetaldehyde.

EXAMPLE 12

Preparation of the Dimethyl Acetal of 2-(N-α-Chloropropionyl-2-methyl-5-chloroanilino)acetaldehyde The dimethyl acetal of 2-(2-methyl-5-chloroanilino)-acetaldehyde (0.1 mole), sodium carbonate (0.06 mole) dissolved in water (50 ml) and benzene (50 ml) are charged into a glass reaction vessel equipped with a mechanical stirrer, thermometer and cooling means. The mixture is cooled to a temperature of about 0° C and α-chloropropionyl chloride (0.11 mole) is incrementally added with stirring. After the addition is completed stirring is continued and the reaction mixture is permitted to warm to room temperature. After this time the mixture is filtered, washed with dilute hydrochloric acid and stripped of solvent to yield the desired product the dimethyl acetal of 2-(N-α-chloropropionyl-2-methyl-5-chloroanilino)-acetaldehyde.

EXAMPLE 13

Preparation of the Dimethyl Acetal of 2-(2-Ethyl-6-methoxyanilino)acetaldehyde

2-Ethyl-6-methoxyaniline (0.3 mole), the dimethyl acetal of 2-chloroacetaldehyde (0.3 mole) and sodium carbonate (20 grams) are charged into a glass reaction vessel equipped with a mechanical stirrer, thermometer and reflux condenser. The reaction mixture is heated at about 150° C for a period of about 8 hours. After this time the mixture is filtered and the filtrate is distilled to yield the desired product the dimethyl acetal of 2-(2-ethyl-6-methoxyanilino)acetaldehyde.

EXAMPLE 14

Preparation of the Dimethyl Acetal of 2-(N-α-Chlorobutanoyl-2-ethyl-6-methoxyanilino)acetaldehyde The dimethyl acetal of 2-(2-ethyl-6-methoxyanilino)-acetaldehyde (0.1 mole), sodium carbonate (0.06 mole) dissolved in water (50 ml) and benzene (50 ml) are charged into a glass reaction vessel equipped with a mechanical stirrer, thermometer and cooling means. The mixture is cooled to a temperature of about 0° C and α-chlorobutanoyl chloride (0.11 mole) is incrementally added with stirring. After the addition is completed stirring is continued and the reaction mixture is permitted to warm to room temperature. After this time the mixture is filtered, washed with dilute hydrochloric acid and stripped of solvent to yield the desired product the dimethyl acetal of 2-(N-α-chlorobutanoyl-2-ethyl-6-methoxyanilino)acetaldehyde.

EXAMPLE 15

Preparation of the Dimethyl Acetal of 2-(2-Propyl-5-fluoroanilino)acetaldehyde

2-Propyl-5-fluoroaniline (0.3 mole), the dimethyl acetal of 2-chloroacetaldehyde (0.3 mole) and sodium carbonate (20 grams) are charged into a glass reaction vessel equipped with a mechanical stirrer, thermometer and reflux condenser. The reaction mixture is heated at about 150° C for a period of about 8 hours. After this time the mixture is filtered and the filtrate is distilled to yield the desired product the dimethyl acetal of 2-(2-propyl-5-fluoroanilino)actaldehyde.

EXAMPLE 16

Preparation of the Dimethyl Acetal of 2-(N-α-Chloroacetyl-2-propyl-5-fluoroanilino)acetaldehyde The dimethyl acetal of 2-(2-propyl-5-fluoroanilino)-acetaldehyde (0.1 mole), sodium carbonate (0.06 mole) dissolved in water (50 ml) and benzene (50 ml) are charged into a glass reaction vessel equipped with a mechanical stirrer, thermometer and cooling means. The mixture is cooled to a temperature of about 0° C and α-chloroacetyl chloride (0.11 mole) is incrementally added with stirring. After the addition is completed stirring is continued and the reaction mixture is permitted to warm to room temperature. After this time the mixture is filtered, washed with dilute hydrochloric acid and stripped of solvent to yield the desired product the dimethyl acetal of 2-(N-α-chloroacetyl-2-propyl-5-fluoroanilino)acetaldehyde.

EXAMPLE 17

Preparation of the Dimethyl Acetal of 2-(2-Methyl-5-cyanoanilino)acetaldehyde 2-Methyl-5-cyanoaniline (0.3 mole), the dimethyl acetal of 2-chloroacetaldehyde (0.3 mole) and sodium carbonate (20 grams) are charged into a glass reaction flask equipped with a mechanical stirrer, thermometer and reflux condenser. The reaction mixture is heated to about 150° C for a period of about 8 hours. After this time the mixture is filtered and the filtrate is distilled to yield the desired product the dimethyl acetal of 2-(2-methyl-5-cyanoanilino)acetaldehyde.

EXAMPLE 18

Preparation of the Dimethyl Acetal of 2-(N-α-Chloroacetyl-2-methyl-5-cyanoanilino)acetaldehyde The dimethyl acetal of 2-(2-methyl-5-cyanoanilino)-acetaldehyde (0.1 mole), sodium carbonate (0.06 mole) dissolved in water (50 ml) and benzene (50 ml) are charged into a glass reaction vessel equipped with a mechanical stirrer, thermometer and cooling means. The mixture is cooled to a temperature of about 0° C and α-chloroacetyl chloride (0.11 mole) is incrementally added with stirring. After the addition is completed stirring is continued and the reaction mixture is permitted to warm to room temperature. After this time the mixture is filtered, washed with dilute hydrochloric acid and stripped of solvent to yield the desired product the dimethyl acetal of 2-(N-α-chloroacetyl-2-methyl-5-cyanoanilino)acetaldehyde.

EXAMPLE 19

Preparation of the Dimethyl Acetal of 2-(2-Methyl-5-methoxyanilino)acetaldehyde 2-Methyl-5-methoxyaniline (0.3 mole), the dimethyl acetal of 2-chloroacetaldehyde (0.3 mole) and sodium carbonate (20 grams) are charged into a glass reaction flask equipped with a mechanical stirrer, thermometer and reflux condenser. The reaction mixture is heated to about 150° C for a period of about 8 hours. After this time the mixture is filtered and the filtrate is distilled to yield the desired product the dimethyl acetal of 2-(2-methyl-5-methoxyanilino)acetaldehyde.

EXAMPLE 20

Preparation of the Dimethyl Acetal of 2-(N-α-Chloroacetyl-2-methyl-5-methoxyanilino)acetaldehyde The dimethyl acetal of 2-(2-methyl-5-methoxyanilino)-acetaldehyde (0.1 mole), sodium carbonate (0.06 mole) dissolved in water (50 ml) and benzene (50 ml) are charged into a glass reaction vessel equipped with a mechanical stirrer, thermometer and cooling means. The mixture is cooled to a temperature of about 0° C and α-chloroacetyl chloride (0.11 mole) is incrementally added with stirring. After the addition is completed stirring is continued and the reaction mixture is permitted to warm to room temperature. After this time the mixture is filtered, washed with dilute hydrochloric acid and stripped of solvent to yield the desired product the dimethyl acetal of 2-(N-α-chloroacetyl-2-methyl-5-methoxyanilino)acetaldehyde.

EXAMPLE 21

Preparation of the Dimethyl Acetal of 2-(2-Methyl-3-methylthioanilino)acetaldehyde 2-Methyl-3-methylthioaniline (0.3 mole), the dimethyl acetal of 2-chloroacetaldehyde (0.3 mole) and sodium carbonate (20 grams) are charged into a glass reaction flask equipped with a mechanical stirrer, thermometer and reflux condenser. The reaction mixture is heated to about 150° C for a period of about 8 hours. After this time the mixture is filtered and the filtrate is distilled to yield the desired product the dimethyl acetal of 2-(2-methyl-3-methylthioanilino)acetaldehyde.

EXAMPLE 22

Preparation of the Dimethyl Acetal of 2-(N-α-Chloroacetyl-2-methyl-3-methylthioanilino)acetaldehyde The dimethyl acetal of 2-(2-methyl-3-methylthioanilino)acetaldehyde (0.1 mole), sodium carbonate (0.06 mole) dissolved in water (50 ml) and benzene (50 ml) are charged into a glass reaction vessel equipped with a mechanical stirrer, thermometer and cooling means. The mixture is cooled to a temperature of about 0° C and α-chloroacetyl chloride (0.11 mole) is incrementally added with stirring. After the addition is completed stirring is continued and the reaction mixture is permitted to warm to room temperature. After this time the mixture is filtered, washed with dilute hydrochloric acid and stripped of solvent to yield the desired product the dimethyl acetal of 2-(N-α-chloroacetyl-2-methyl-3-methylthioanilino)acetaldehyde.

EXAMPLE 23

Preparation of the Dimethyl Acetal of 2-(2-Methyl-5trifluoromethylanilino)acetaldehyde 2-Methyl-5-trifluoromethylaniline (0.3 mole), the dimethyl acetal of 2-chloroacetaldehyde (0.3 mole) and sodium carbonate (20 grams) are charged into a glass reaction flask equipped with a mechanical stirrer, thermometer and reflux condenser. The reaction mixture is heated to about 150° C for a period of about 8 hours. After this time the mixture is filtered and the filtrate is distilled to yield the desired product the dimethyl acetal of 2-(2-methyl-5-trifluoromethylanilino)acetaldehyde.

EXAMPLE 24

Preparation of the Dimethyl Acetal of 2-(N-α-Chloroacetyl-2-methyl-5-trifluoromethylanilino)acetaldehyde The dimethyl acetal of 2-(2-methyl-5-trifluoromethylanilino)acetaldehyde (0.1 mole), sodium carbonate (0.06 mole) dissolved in water (50 ml) and benzene (50 ml) are charged into a glass reaction vessel equipped with a mechanical stirrer, thermometer and cooling means. The mixture is cooled to a temperature of about 0° C and α-chloroacetyl chloride (0.11 mole) is incrementally added with stirring. After the addition is completed stirring is continued and the reaction mixture is permitted to warm to room temperature. After this time the mixture is filtered, washed with dilute hydrochloric acid and stripped of solvent to yield the desired product the dimethyl acetal of 2-(N-α-chloroacetyl-2-methyl-5-trifluoromethylanilino)-acetaldehyde.

EXAMPLE 25

Preparation of the Dimethyl Acetal of 2-(2-Methyl-5-methoxymethylanilino)acetaldehyde 2-Methyl-5-methoxymethylaniline (0.3 mole), the dimethyl acetal of 2-chloroacetaldehyde (0.3 mole) and sodium carbonate (20 grams) are charged into a glass reaction flask equipped with a mechanical stirrer, thermometer and reflux condenser. The reaction mixture is heated to about 150° C for a period of about 8 hours. After this time the mixture is filtered and the filtrate is distilled to yield the desired product the dimethyl acetal of 2-(2-methyl-5-methoxymethylanilino)acetaldehyde.

EXAMPLE 26

Preparation of the Dimethyl Acetal of 2-(N-α-Chloroacetyl-2-methyl-5-methoxymethylanilino)acetaldehyde The dimethyl acetal of 2-(2-methyl-5-methoxymethylanilino)acetaldehyde (0.1 mole), sodium carbonate (0.06 mole) dissolved in water (50 ml) and benzene (50 ml) are charged into a glass reaction vessel equipped with a mechanical stirrer, thermometer and cooling means. The mixture is cooled to a temperature of about 0° C and α-chloroacetyl chloride (0.11 mole) is incrementally added with stirring. After the addition is completed stirring is continued and the reaction mixture is permitted to warm to room temperature. After this time the mixture is filtered, washed with dilute hydrochloric acid and stripped of solvent to yield the desired product the dimethyl acetal of 2-(N-α-chloroacetyl-2-methyl-5-methoxymethylanilino)-acetaldehyde.

Additional exemplary compounds within the scope of the present invention which can be prepared by the procedures of the foregoing examples are the dimethyl acetal of 2-(N-α-chloroacetyl-2,6-dipropylanilino)acetaldehyde, the diethyl acetal of 2-(N-α-bromoacetyl-2,6-dibutylanilino)acetaldehyde, the dipropyl acetal of 2-(N-α-iodoacetyl-2,6-dipentylanilino)-acetaldehyde, the dibutyl acetal of 2-(N-α-chloropropionyl-2,6-dihexylanilino)acetaldehyde, the dipentyl acetal of 2-(N-α-chlorobuanoyl-2-methyl-6-ethoxyanilino)acetaldehyde, the dihexyl acetal of 2-(N-α-chloropentanoyl-2methyl-6-propoxyanilino)acetaldehyde, the methyl ethyl acetal of 2-(N-α-chlorohexanoyl-2-methyl-6-butoxyanilino)acetaldehyde, the methyl propyl acetal of 2-(N-α-chloroheptanoyl)-2-methyl-6-hexyloxyanilino)acetaldehyde, the ethyl propyl acetal of 2-(N-α-bromoacetyl-2-methyl-5-bromoanilino)acetaldehyde, the dimethyl acetal of 2-(N-α-chloroacetyl-2-methyl-5-iodoanilino)acetaldehyde, the dimethyl acetal of 2-(N-α-chloroacetyl-2-ethyl-3-fluoroanilino)acetaldehyde, the dimethyl acetal of 2-(N-α-chloroacetyl-2-methyl-3-ethylanilino)-acetaldehyde, the dimethyl acetal of 2-(N-α-chloroacetyl-2,3,6-triethylanilino)acetaldehyde, the dimethyl acetal of 2-(N-α-chloroacetyl-2-methyl-5-ethylanilino)acetaldehyde, the dimethyl acetal of 2-(N-α-chloroacetyl-2-methyl-5-hexylanilino)acetaldehyde, the dimethyl acetal of 2-(N-α-chloroacetyl-2-methyl-3-propylanilino)acetaldehyde, the dimethyl acetal of 2-(N-α-chloroacetyl-2,6-dimethyl-3-butylanilino)acetaldehyde, the dimethyl acetal of 2-(N-α-chloroacetyl-2,6-dimethyl-3-hexylanilino)acetaldehyde, the dimethyl acetal of 2-(N-α-chloroacetyl-2,6-dimethyl-3-ethoxyanilino)acetaldehyde, the dimethyl acetal of 2-(N-α-chloroacetyl-2,6-dimethyl-3-propoxyanilino)acetaldehyde, the dimethyl acetal of 2-(N-α-chloroacetyl-2,6-dimethyl-3-butyloxyanilino)acetaldehyde, the dimethyl acetal of 2-(N-α-chloroacetyl-2,6-dimethyl-3-hexyloxyanilino)acetaldehyde, the dimethyl acetal of 2-(N-α-chloroacetyl-2,6-dimethyl-3-methylthioanilino)acetaldehyde, the dimethyl acetal of 2-(N-α-chloroacetyl-2,6-dimethyl-3-ethylthioanilino)acetaldehyde, the dimethyl acetal of 2-(N-α-chloroacetyl-2,6-dimethyl-3-propylthioanilino)acetaldehyde, the dimethyl acetal of 2-(N-α-chloroacetyl-2,6-dimethyl-3-hexylthioanilino)acetaldehyde, the dimethyl acetal of 2-(N-α-chloroacetyl-2,6-dimethyl-3-chloromethylanilino)acetaldehyde, the dimethyl acetal of 2-(N-α-chloroacetyl-2,6-dimethyl-3-bromomethylanilino)acetaldehyde, the dimethyl acetal of 2-(N-α-chloroacetyl-2,6-dimethyl-3-β-bromoethylanilino)acetaldehyde, the dimethyl acetal of 2-(N-α-chloroacetyl-2,6-dimethyl-3-γ-chloropropylanilino)acetaldehyde, the dimethyl acetal of 2-(N-α-chloroacetyl-2,6-dimethyl-3-methoxymethylanilino)acetaldehyde, the dimethyl acetal of 2-(N-α-chloroacetyl-2,6-dimethyl-3-β-mehoxyethylanilino)acetaldehyde, the dimethyl acetal of 2-(N-α-chloroacetyl-2,6-dimethyl-3-γ-methoxypropylanilino)acetaldehyde, the dimethyl acetal of 2-(N-α-chloroacetyl-2,6-dimethyl-3-ethoxymethylanilino)acetaldehyde, the dimethyl acetal of 2-(N-α-chloroacetyl-2,6-dimethyl-3-propoxymethylanilino)acetaldehyde, the dimethyl acetal of 2-(N-α-chloroacetyl-2,6-dimethyl-3-butyloxymethylanilino)-acetaldehyde and the like.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wetable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

Example 27

| Preparation of a Dust | |
|---|---|
| Product of Example 2 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atazine, trietazine, simetone, prometone, propazine, ametryne and the like; chloroacetamide herbicides such as 4-(chloroacetyl)morpholine, 1-(chloroacetyl)- piperidine and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamide, dipropalin, triflualin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morningglory, bedstraw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, wintercress, horsenettle, nutsedge, milkweed and sicklepod.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively non-toxic to many beneficial plants. The exact amount of compound required will depend on a variety of factors, including the hardiness of the particular weed species, weather, type of soil, method of application, the kind of beneficial plants in the same area, and the like. Thus, while the application of up to only about 1 or 2 ounces of active compound per acre may be sufficient for good control of a light infestation of weeds growing under adverse conditions, the application of 10 pounds or more of an active compound per acre may be required for good control of a dense infestation of hardy perennial weeds growing under favorable conditions.

required and daily or more frequent watering. The plants were maintained under these conditions for a period of from 15 to 21 days, at which time the condition of the plants and the degree of injury to the plants was rated on a scale of from 0 to 10, as follows: 0 = no injury, 1,2 = slight injury, 3,4 = moderate injury, 5,6 = moderately severe injury, 7,8,9 = severe injury and 10 = death. The effectiveness of these compounds is demonstrated by the following data:

TABLE I

| Test Compound | Concentration (lbs./acre) | INJURY RATING Weed Species | | | | | | | | | | | |
|---|---|---|---|---|---|---|---|---|---|---|---|---|
| | | YNSG | WOAT | JMWD | VTLF | JNGS | PIGW | MSTD | YLFX | BNGS | CBGS | CTGS | MNGY |
| Product of Example 2 | 10 | 10 | 9 | 7 | 6 | 9 | 10 | 7 | 10 | 10 | 10 | 10 | 6 |
| | 4 | 10 | — | — | — | 10 | — | — | 9 | 10 | 10 | 10 | — |
| | 2 | 10 | — | — | — | 8 | — | — | 9 | 10 | 9 | 10 | — |
| | 1 | 10 | — | — | — | 3 | — | — | 6 | 10 | 8 | 10 | — |
| Product of Example 4 | 10 | 10 | 2 | 0 | 0 | 7 | 9 | 0 | 9 | 10 | 9 | 8 | 0 |
| | 4 | 7 | — | — | — | 4 | — | — | 3 | 10 | 8 | 1 | — |
| | 2 | 10 | — | — | — | 0 | — | — | 4 | 9 | 4 | 0 | — |
| | 1 | 9 | — | — | — | 0 | — | — | 0 | 8 | 1 | 0 | — |
| Product of Example 6 | 10 | 10 | 9 | 2 | 1 | 10 | 10 | 3 | 10 | 10 | 10 | 10 | 0 |
| | 4 | 10 | — | — | — | 5 | — | — | 8 | 10 | 9 | 5 | — |
| | 2 | 10 | — | — | — | 4 | — | — | 7 | 9 | 8 | 1 | — |
| | 1 | 10 | — | — | — | 3 | — | — | 1 | 6 | 3 | 0 | — |
| Product of Example 8 | 10 | 10 | 3 | 0 | 0 | 9 | 10 | 3 | 9 | 10 | 10 | 10 | 3 |
| | 4 | 10 | — | — | — | 9 | — | — | 8 | 10 | 8 | 2 | — |
| | 2 | 10 | — | — | — | 6 | — | — | 5 | 10 | 8 | 0 | — |
| | 1 | 7 | — | — | — | 2 | — | — | 2 | 10 | 4 | 0 | — |

YNSG = Yellow Nutsedge
WOAT = Wild Oats
JMWD = Jimsonweed
VTLF = Velvetleaf
JNGS = Johnsongrass
PIGW = Pigweed
MSTD = Mustard
YLFX = Yellow Foxtail
BNGS = Barnyardgrass
CBGS = Crabgrass
CTGS = Cheatgrass
MNGY = Morningglory The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after seeding the pots were sprayed with water until the soil was wet and the test compounds formulated as aqueous emulsions of acetone solutions containing emulsifiers were sprayed at the indicated concentrations on the surface of the soil.

The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the weeds that have attained a prescribed size. After spraying the plants were placed in a greenhouse and watered daily or more frequently. Water was not applied to the foliage of the treated plants. The severity of the injury was determined 10 to 15 days after treatment and was rated on the scale of from 0 to 10 heretofore described. The effectiveness of these compounds is demonstrated by the following data:

TABLE II

| Test Compound | Concentration (lbs./acre) | INJURY RATING Weed Species | | | | | | | | | | | |
|---|---|---|---|---|---|---|---|---|---|---|---|---|
| | | YNSG | WOAT | JMWD | PIGW | JNGS | BDWD | MSTD | YLFX | BNGS | CBGS | MNGY | CTGS |
| Product of Example 2 | 10 | 7 | 6 | 8 | 10 | 8 | 8 | 10 | 9 | 9 | 10 | 7 | — |
| | 4 | 6 | — | — | — | 6 | — | — | 8 | 9 | 8 | — | 8 |
| | 2 | 6 | — | — | — | 6 | — | — | 8 | 9 | 8 | — | 8 |
| | 1 | 8 | — | — | — | 5 | — | — | 8 | 9 | 8 | 5 | 8 |
| Product of Example 4 | 10 | 6 | 4 | 2 | 10 | 9 | 7 | 5 | 9 | 8 | 9 | — | 7 |
| | 4 | 3 | — | — | — | 2 | — | — | 9 | 9 | 4 | — | 4 |
| | 2 | 3 | — | — | — | 0 | — | — | 8 | 9 | 4 | — | 2 |
| | 1 | 2 | — | — | — | 0 | — | — | 2 | 9 | 1 | — | 2 |
| Product of Example 6 | 10 | 8 | 5 | 4 | 10 | 5 | 8 | 9 | 9 | 9 | 9 | 8 | — |
| | 4 | 9 | — | — | — | 7 | — | — | 8 | 9 | 9 | — | 7 |
| | 2 | 6 | — | — | — | 3 | — | — | 8 | 9 | 7 | — | 8 |
| | 1 | 7 | — | — | — | 1 | — | — | 3 | 8 | 6 | 3 | 6 |
| Product of Example 8 | 10 | 8 | 7 | 6 | 9 | 8 | 9 | 7 | 9 | 9 | 9 | — | — |
| | 4 | 8 | — | — | — | 6 | — | — | 8 | 9 | 8 | — | 6 |
| | 2 | 7 | — | — | — | 2 | — | — | 7 | 7 | 6 | — | 4 |
| | 1 | 5 | — | — | — | 0 | — | — | 5 | 7 | 3 | — | 1 |

YNSG = Yellow Nutsedge
WOAT = Wild Oats
JMWD = Jimsonweed
PIGW = Pigweed
JNGS = Johnsongrass
BDWD = Bindweed
MSTD = Mustard
YLFX = Yellow Foxtail
BNGS = Barnyardgrass
CBGS = Crabgrass
MNGY = Morningglory
CTGS = Cheatgrass After spraying, the soil containers were placed in the greenhouse and provided with supplementary heat as

I claim:

1. A herbicidal composition comprising an inert carrier and, as an essential active ingredient, in a quantity toxic to weeds, a compound of the formula

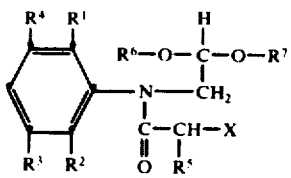

wherein $R^1$, $R^6$ and $R^7$ are each lower alkyl; $R^2$ is selected from the group consisting of hydrogen, lower alkyl, and lower alkoxy; $R^3$ and $R^4$ are each selected from the group consisting of hydrogen, lower alkyl, halogen, cyano, lower alkoxy, lower alkylthio, lower chloroalkyl, trifluoromethyl and lower alkoxyalkyl; $R^5$ is selected from the group consisting of hydrogen and lower alkyl; and X is selected from the group consisting of chlorine and bromine.

2. The composition of claim 1 wherein the compound is the dimethyl acetal of 2-(N-α-chloroacetyl-2,6-dimethylanilino)acetaldehyde.

3. The composition of claim 1 wherein the compound is the diethyl acetal of 2-(N-α-chloroacetyl-2,6-diethylanilino)acetaldehyde.

4. The composition of claim 1 wherein the compound is the diethyl acetal of 2-(N-α-chloroacetyl-2,6-dimethylanilino)acetaldehyde.

5. The composition of claim 1 wherein the compound is the dimethyl acetal of 2-(N-α-chloroacetyl-2,6-diethylanilino)acetaldehyde.

6. The composition of claim 1 wherein the compound is the dimethyl acetal of 2-(N-α-bromopropionyl-2,3,6-trimethylanilino)acetaldehyde.

7. The composition of claim 1 wherein the compound is the dimethyl acetal of 2-(N-α-chloropropionyl-2-methyl-5-chloroanilino)acetaldehyde.

8. The composition of claim 1 wherein the compound is the dimethyl acetal of 2-(N-α-chlorobutanoyl-2-ethyl-6-methoxyanilino)acetaldehyde.

9. A method of controlling weeds which comprises contacting the weeds with a herbicidal composition of claim 1.

* * * * *